United States Patent
Smits et al.

(10) Patent No.: US 7,133,715 B1
(45) Date of Patent: Nov. 7, 2006

(54) HEARING EVALUATION DEVICE WITH NOISE DETECTION AND EVALUATION CAPABILITY

(75) Inventors: Matthijs P. Smits, Woodside, CA (US); Bryan P. Flaherty, Half Moon Bay, CA (US)

(73) Assignee: Natus Medical Inc., San Carlos, CA (US)

( * ) Notice: Subject to any disclaimer, the term of this patent is extended or adjusted under 35 U.S.C. 154(b) by 0 days.

(21) Appl. No.: 09/479,548

(22) Filed: Jan. 7, 2000

(51) Int. Cl.
*A61B 5/04* (2006.01)
*H04R 29/00* (2006.01)

(52) U.S. Cl. .................. 600/544; 600/559; 600/300; 600/378; 381/60

(58) Field of Classification Search ............... 381/60; 600/559, 300, 544
See application file for complete search history.

(56) References Cited

U.S. PATENT DOCUMENTS

| | | | | |
|---|---|---|---|---|
| 4,275,744 A | * | 6/1981 | Thornton et al. | 600/544 |
| 4,308,873 A | | 1/1982 | Maynard | 600/554 |
| 4,375,744 A | * | 3/1983 | Briner et al. | 57/96 |
| 4,493,327 A | * | 1/1985 | Bergelson et al. | 600/544 |
| 4,545,388 A | | 10/1985 | John | 600/544 |
| 5,003,986 A | * | 4/1991 | Finitzo et al. | 600/544 |
| 5,099,856 A | * | 3/1992 | Killion et al. | 600/544 |
| 5,226,496 A | * | 7/1993 | Feinland et al. | 177/25.15 |
| 5,230,344 A | * | 7/1993 | Ozdamar et al. | 600/544 |
| 5,368,041 A | | 11/1994 | Shambroom | 128/731 |
| 5,413,114 A | | 5/1995 | Zurek et al. | 600/559 |
| 5,601,091 A | * | 2/1997 | Dolphin | 600/559 |
| 5,697,379 A | * | 12/1997 | Neely et al. | 600/544 |
| 5,792,072 A | * | 8/1998 | Keefe | 600/559 |
| 5,916,174 A | | 6/1999 | Dolphin | 600/559 |
| 5,954,667 A | * | 9/1999 | Finkenzeller et al. | 600/544 |
| 5,964,667 A | | 10/1999 | Brookman | 743/176 |
| 5,999,856 A | | 12/1999 | Kennedy | 600/559 |
| 6,071,246 A | | 6/2000 | Sturzebecher et al. | 600/599 |
| 6,080,112 A | | 6/2000 | Don | 600/599 |
| 6,110,126 A | * | 8/2000 | Zoth et al. | 600/559 |
| 6,343,230 B1 | * | 1/2002 | Smits et al. | 600/544 |
| 6,475,163 B1 | * | 11/2002 | Smits et al. | 600/559 |
| 6,620,100 B1 | * | 9/2003 | Smits et al. | 600/300 |

OTHER PUBLICATIONS

Don, M. Evaluating residual background noise in human auditory brain-stem responses. Journal of Acoustical Society of America. 96 (5), Nov. 1994.*

M. Don and C. Elberling, *Evaluating Residual Background Noise in Human Auditory Brain-Stem Responses*, J. Acoust. Soc. Am. 96 (5), (1994) Pt. 1: 2746-2757.

* cited by examiner

*Primary Examiner*—Vivian Chin
*Assistant Examiner*—Devona E. Faulk
(74) *Attorney, Agent, or Firm*—Mathew J. Temmerman

(57) ABSTRACT

An apparatus and method for evaluation of hearing loss is disclosed. The apparatus and method use evoked Auditory Brainstem Responses (ABR) to determine if the subject is able to hear click stimuli that are repeatedly administered. In order to facilitate efficient differentiation of the ABR from the accompanying noise, normative data is used to detect test conditions where physiological, non-physiological, and ambient acoustic noise would interfere with the progression of test.

17 Claims, 6 Drawing Sheets

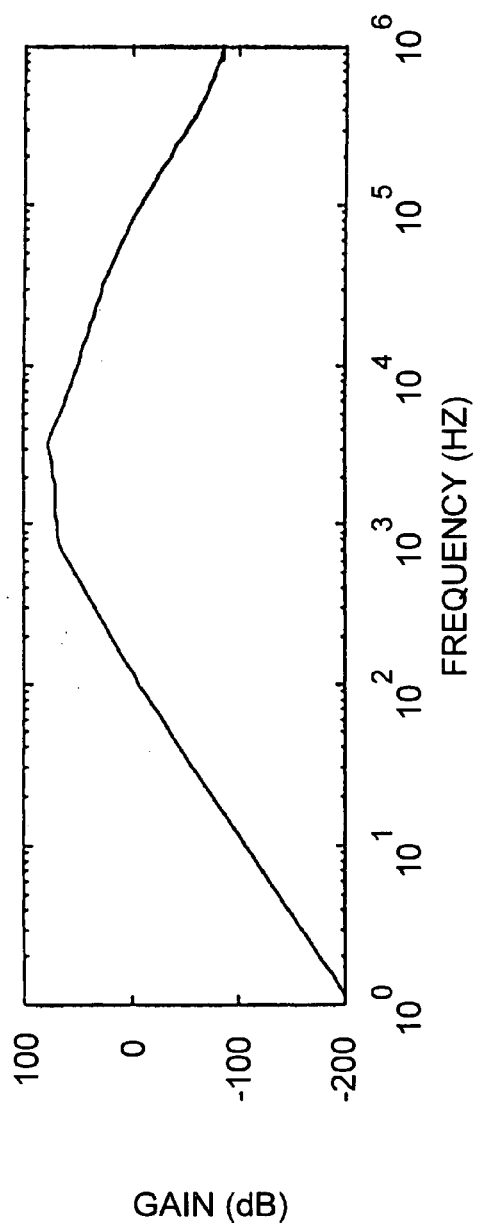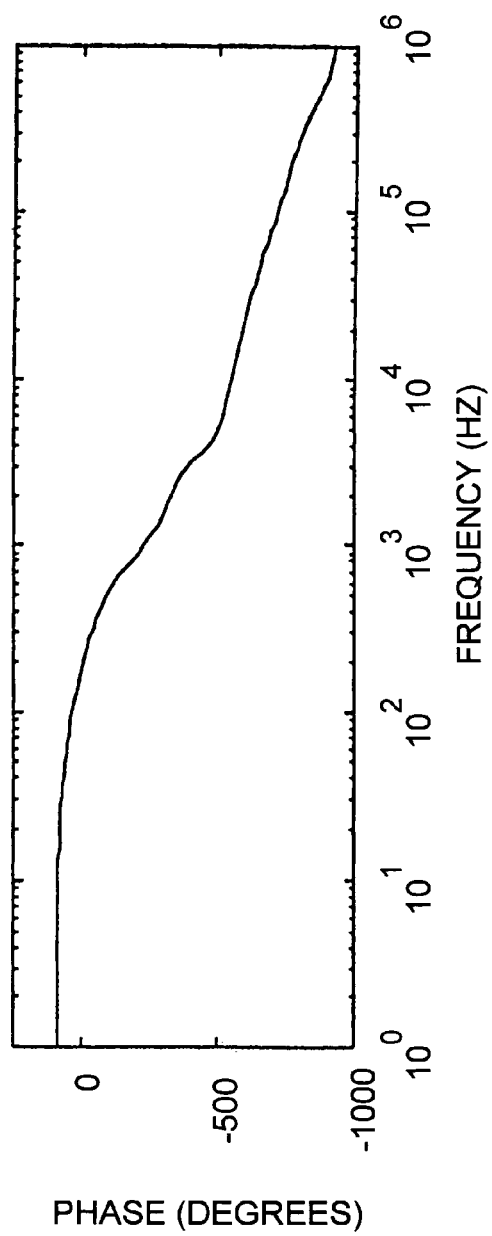

HEARING EVALUATION DEVICE WITH NOISE DETECTION AND EVALUATION CAPABILITY

RELATED APPLICATIONS

This application is related to the co-pending and commonly assigned U.S. patent application Ser. No. 09/479,559, entitled "Hearing Evaluation Device with Patient Connection Evaluation Capabilities," filed by Matthijs P. Smits, Vineet Bansal, Abraham J. Totah and Bryan P. Flaherty and the U.S. patent application Ser. No. 09/479,557, entitled "Hearing Evaluation with predictive Capabilities," filed by Matthijs P. Smits and Christopher M. Coppin, the disclosures of which are hereby incorporated herein by reference.

FIELD OF THE INVENTION

The present invention relates to devices and methods that use electroencephalographic responses to auditory stimuli to evaluate hearing loss. More particularly, the present invention relates to the detection and evaluation of excessive noise factors, thereby increasing the reliability and speed of such evaluation.

BACKGROUND OF THE INVENTION

In the past, hearing impairment in babies and children was often not detected until after it was observed that the baby or child did not respond normally to sound. Unfortunately, it often took months or even years for the parent to observe the impairment, and by that time the child's language and learning abilities were negatively and often irreversibly impacted. Indeed, recent studies indicate that the vocabulary skills of hearing impaired children markedly increases if their hearing loss is detected early. The optimal time to evaluate for hearing loss is thus immediately after birth, both because early detection allows for early treatment, and because parents often fail to bring their infants for later appointments. As a result, a number of states have implemented programs to evaluate newborns for hearing loss.

However, babies, especially newborns, cannot participate in traditional hearing tests, which require the subject to indicate if he or she hears the auditory stimulus. Thus, devices and methods have been developed to objectively determine hearing loss, without the voluntary participation of the subject. One such method involves analysis of the involuntary electroencephalographic (EEG) signals that are evoked from a subject in response to an auditory stimulus. It has been found that when a subject is able to perceive a sound having particular characteristics, a specific EEG waveform known as an Auditory Brainstem Response (ABR) is generated. This ABR response signal is typically small in magnitude in relation to general EEG activity. Therefore, statistical and signal processing techniques have been employed and developed to help detect, to a pre-defined level of statistical confidence, whether an ABR response has in fact been evoked. ABR testing is especially applicable to evaluation of infants, but can be applied to any subject.

The ABR that is evoked in response to the auditory stimulus may be measured by use of surface electrodes on the scalp or neck. As a practical matter, the electrodes will also detect noise signals from neural activity (besides the ABR), muscle activity, and non-physiological, environmental noises. Accurate detection of excessive noise, and excessive non-physiological noise, has thus been a challenge for those developing ABR evaluation tests. It would be especially advantageous to discern non-physiological noise, because such noise may be ameliorated or even eliminated (such as by moving or turning off an interfering device).

The present invention represents a major advance in the art because it allows for more accurate detection of excessive noise, and because it provides a method to detect non-physiological noise.

DESCRIPTION OF THE PRIOR ART

Several techniques have been used to minimize the physiological noise in the EEG response from an auditory stimulus (see M. Don and C. Elberling, *Evaluating Residual Background Noise in Human Auditory Brain-Stem Responses*, J. Acoust. Soc. Am. 96 (5), Pt. 1:2746–2757 (1994)), including signal averaging and weighted signal averaging, signal filtering, artifact rejection, stimulus modification, targeted electrode placement, and various techniques designed to relax or sedate the subject.

The prior art also details techniques that evaluate the current noise content in the averaged EEG response against a pre-set threshold, which represents a stopping criterion for the hearing loss evaluation. However, the prior art does not provide for the detection of excessive noise in relation to non-physiological noise sources or the use of normative data.

The prior art also addresses some excessive acoustic noise issues by rejecting EEG responses if the ambient acoustic noise amplitude exceeds a certain pre-set threshold. Such ambient acoustic noise can be detected from a microphone placed on or near the earphones of the subject, and if it exceeds a predetermined voltage threshold, then EEG responses obtained at or near the time of excessive noise can be rejected. Additionally, the ambient noise received by the microphones can be filtered before analysis, to exclude noise that is unlikely to interfere with testing by masking the auditory click stimulus.

OBJECTS AND SUMMARY OF THE INVENTION

The present invention provides a device and method for use in analyzing the EEG signal evoked in response to an auditory click stimulus, to determine if the subject suffers from hearing loss. Broadly, the invention is directed to devices and methods that are capable of detecting excessive noise, based upon analysis using normative data, and using certain statistical techniques. This invention also is directed to devices and methods capable of detecting certain non-physiological noise, and determining when such non-physiological noise is excessive. Additionally, this invention allows for an improved determination of whether the ambient acoustic noise in the test site is excessive.

In one embodiment of the invention, evoked EEG responses to auditory stimuli are collected, and organized into "sweeps," with each sweep containing the response signal for one auditory stimulus. The sweeps are organized into blocks, with each block containing a number of sweeps.

The response signal for each sweep is digitized and converted into a series of binary numbers corresponding to whether the amplitude of the response signal is positive or negative at various points in time. The digitized, binary waveform is compared to a benchmark ABR waveform to determine if the ABR is present. To make this determination, polarity sum is calculated, which represents the sum of the polarities of the response signals at each measured point in time. Statistical techniques are then used to determine if an ABR is present, relying upon the expected distribution of polarity sums in the absence of an ABR. A "Pass" is triggered if the observed polarity sum distribution is determined to be statistically different, to a defined threshold, than that expected from random noise. After a certain number of blocks have been completed, the evaluation will cease if a "Pass" has yet not been triggered. Under such circumstances, the subject will be referred for further testing to determine if he or she in fact does suffer from hearing loss.

In accordance with the present invention, evaluation may be paused if the noise contribution to the response signal exceeds a preset threshold, and therefore is deemed to be excessive. The preset threshold is preferably derived from an analysis with standardized normative data. The pause period allows the operator time to attempt to correct the excessive noise. Moreover, evaluation can also be paused if the contribution of non-physiological noise is excessive. One method of determining excessive non-physiological noise is to measure the extent to which the average sum of polarities deviates from chance, i.e., the extent to which the distribution of the average sum of polarities deviates from the distribution that would be expected. Another method of determining excessive non-physiological noise is to measure the difference between the mean and median EEG signal amplitude for a block of sweeps. If such deviation or difference is beyond a pre-set threshold (and therefore "excessive"), the evaluation may not only pause to allow the operator an opportunity to correct the problem, but the latest block of data may also be rejected.

It may be desirable in some instances to alert the operator to the presence of non-physiological noise even if the noise is not deemed to be excessive. The operator could then attempt to ameliorate or even eliminate the noise, thereby increasing the efficiency of the test. The present invention therefore improves upon the prior art through its methods of automatically detecting excessive noise, and by detecting an excessive non-physiological component in the noise.

The present invention also provides an improved device and method to determine if the ambient acoustic noise is excessive, based upon signal energy, rather than noise amplitude, as commonly used in artifact rejection.

As described below, the present invention makes extensive use of normative data. These normative data were derived from analysis of clinical data, and from computer simulations representing different testing conditions. Normative data have been used to develop the drawings described in the subsequent paragraph, and are thus representative of clinical and statistical (computer simulated) data that could be compiled by a person of ordinary skill in the art.

BRIEF DESCRIPTION OF THE DRAWINGS

Further features, elements, and advantages of the present invention will become apparent to a person of ordinary skill in the art in view of the following detailed description of a preferred embodiment of the present invention, made with reference to the drawings annexed, in which like reference characters correspond to like elements, and in which:

FIG. 5 illustrates a bode plot of the hardware filtering for the ambient noise evaluation.

Figure 1:
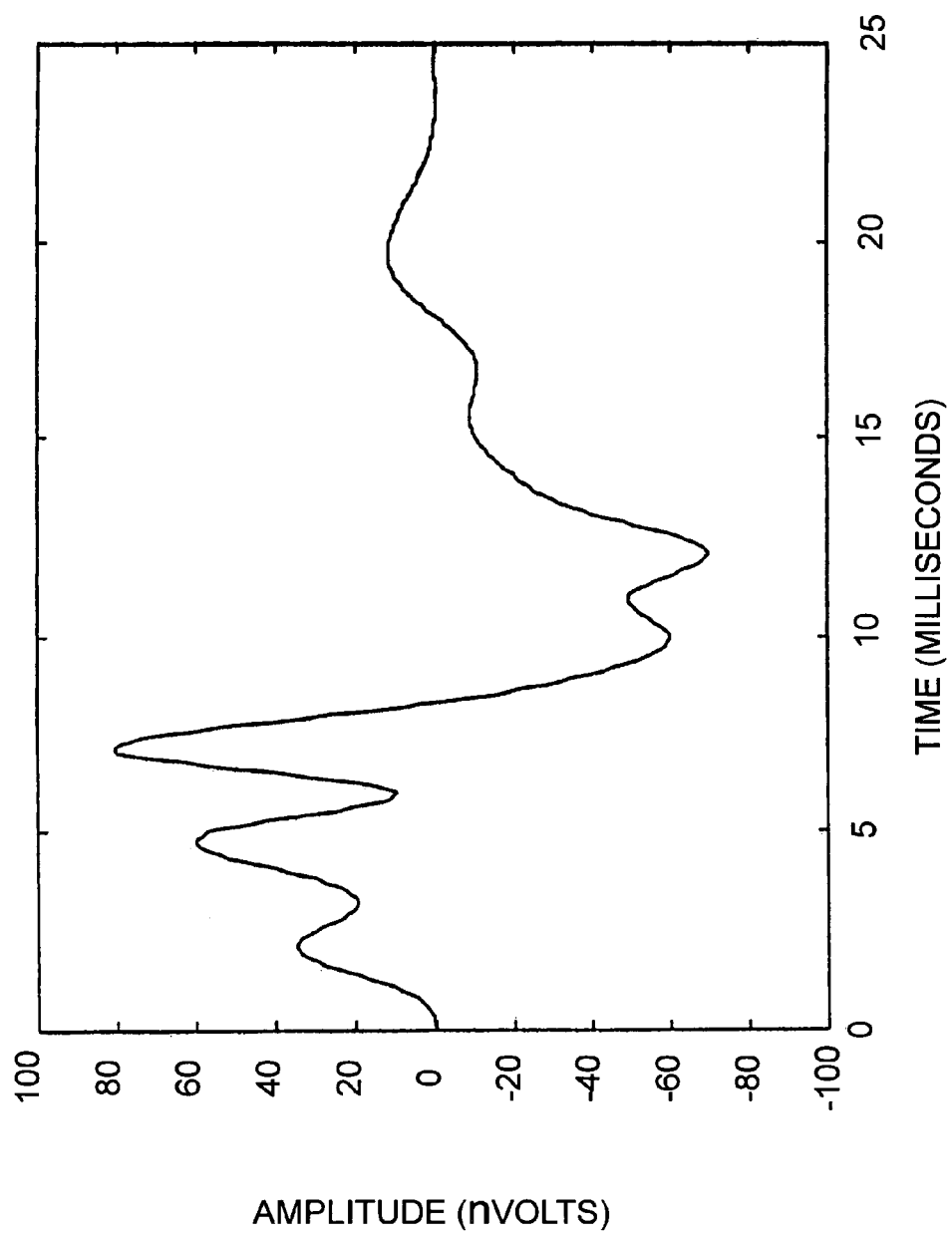
FIG. 1 illustrates a typical ABR waveform.

DESCRIPTION OF THE PREFERRED EMBODIMENT a. Overview

The invention disclosed herein detects, processes and analyzes the EEG response of a subject to certain sound stimuli. A click sound stimulus is repetitively applied to the subject's ear through a transducer. The click stimuli may be applied to one ear at a time (monoaurally), or to both ears simultaneously (binaurally). In a preferred embodiment, monoaural stimuli are applied at 37 Hz.

The EEG response is detected from surface electrodes. Testing may be performed to ensure that the electrodes have been properly placed, and that nothing is impeding the electrodes' ability to detect the EEG response signal.

In a preferred embodiment (see FIG. 6), the electrodes are placed on the subject in the following manner: a positive electrode is placed on the forehead, a negative electrode is placed on the nape of the neck, and a ground electrode is placed on the mastoid or shoulder. The EEG signal detected from these electrodes is filtered so as to exclude signals that are not applicable to the ABR.

The amplitude of the EEG response is digitized, and is assigned a binary value. This binary value represents the amplitude polarity of the waveform, that is, whether the response EEG amplitude is positive or negative, at the measured time.

The stimuli and responses are grouped into "sweeps" and "blocks." A sweep is a response waveform to a single click stimulus. A block is a series of sweeps, and in a preferred embodiment, represents 500 accepted click stimulus responses. We refer to "accepted" click stimulus responses, because results from some sweeps may be rejected from analysis due to problems with the testing conditions, as explained further below.

Upon completion of a block of accepted sweeps, signal averaging is used to compute the composite waveform that results from this block. In addition, signal averaging is also used to compute the average composite waveform from all blocks combined. This average composite waveform is then compared with an internal template, to determine if the null hypothesis ($H_0$) can be rejected. The null hypothesis is the hypothesis that the baby is hearing-impaired (i.e., there is no ABR response), and will be rejected if the probability of hearing impairment is below a certain pre-set statistical threshold. In the preferred embodiment, the null hypothesis is rejected, and the evaluation ceases, when sufficient data has been collected to conclude, with 99.96% statistical confidence, that an ABR waveform is present. A "PASS" or other similar message may then be generated.

If the average composite waveform is insufficient to reject the null hypothesis, then the evaluation continues until the total number of sweeps exceeds a preset threshold. If the maximum number of sweeps has been exceeded, but the null hypothesis has not been rejected, then the subject would typically be referred for further testing to determine if in fact he or she suffers from hearing impairment. Additionally, for certain subjects, the present invention may be able to predict that the subject will not pass, thus obviating the need for lengthy testing. (See U.S. patent application entitled "Hearing Evaluation Device with Predictive Capabilities," filed by Matthijs P. Smits and Christopher M. Coppin).

b. Signal Analysis

Figure 3A:
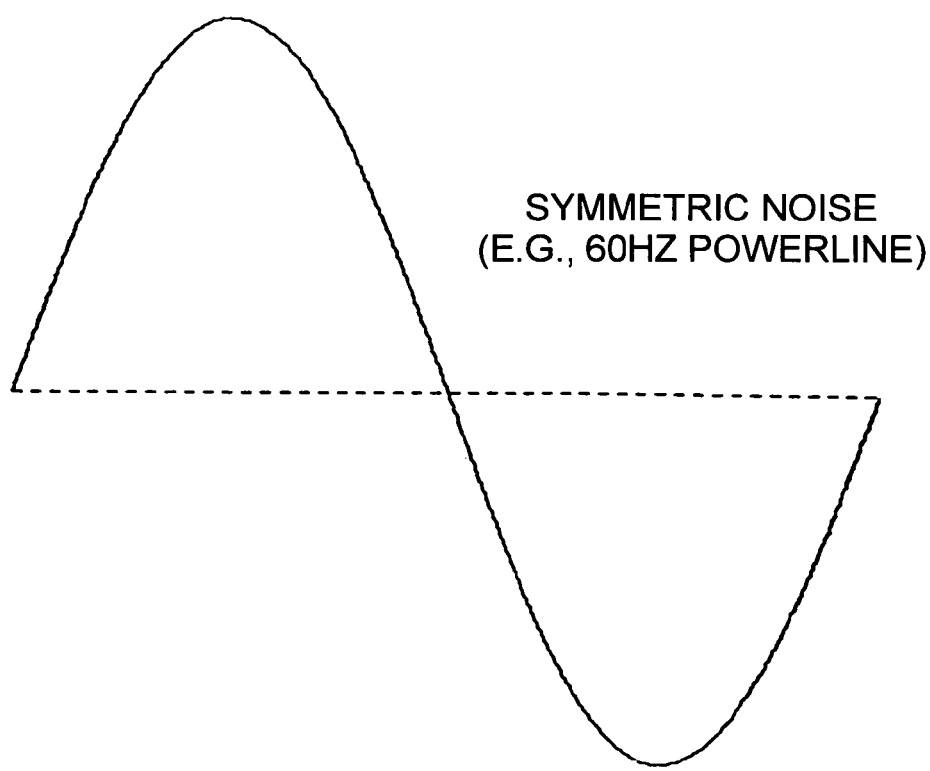
FIG. 3 illustrates examples of typical symmetric 60 Hz noise and asymmetric 60 Hz monitor refresh pulse noise.
Figure 3B:
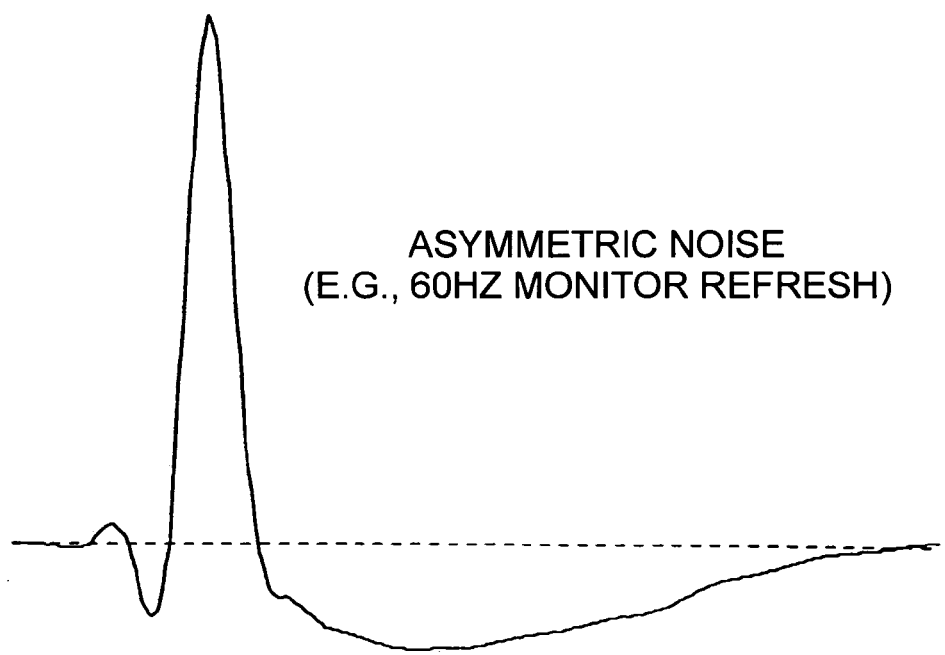

The chief challenge in using ABR to evaluate for hearing loss is the difficulty in distinguishing the ABR response (if any) from the noise within which it is buried. This noise is typically Gaussian-distributed, with a mean amplitude of zero, and with changing variance. Additionally, certain non-physiological noise is distinguished by the fact that it is asymmetric, as illustrated in FIG. 3, which shows a typical symmetrical 60 Hz noise, and the asymmetrical noise associated with the refresh function of a computer monitor.

As stated above, the present invention detects the presence of an ABR by repetitively applying click stimuli in blocks of $N_b=500$ sweeps. Each click stimulus is comprised of a brief acoustic pulse containing energy primarily in the 500–4000 Hz region. The repetition rate for the clicks is 37 Hz. The polarities of the click stimuli are sequentially alternated between condensation (positive square pulse) and rarefaction (negative square pulse) stimuli. Since the noise typically has a mean of zero and no component is asynchronous with the stimulus repetition rates, it is likely to sum toward zero with increasing sweeps, leaving the ABR.

Under the preferred embodiment of the present invention, the amplitude sequence of each click stimulus response is converted into a sequence of polarities (positive or negative) which, in turn, is summed with the other response polarity sequences in block b, to form the array $X_b$. For instance, an amplitude sample in the click stimulus response would be given a "1" if this amplitude were positive (no matter how high), and a "0" if this amplitude were negative (no matter how low). And, if no ABR were present the expected proportion of polarities, which is the same as the polarities of the ABR waveform would be 0.5. However, if an ABR were present, the proportion would likely be higher. The proportion of polarities in an evoked response matching the ABR waveform is related to the amount of signal noise.

After each block of sweeps, the summed polarity sequence $X_b$ for block b is summed with the other summed polarity sequences into an array X. Also, the total number of sweeps N is calculated as the sum of the number of sweeps in each block:

$$\begin{cases} X = \sum_{b=1}^{B} X_b \\ \qquad\qquad b = 1, 2, \ldots, B \\ N = \sum_{b=1}^{B} N_b \end{cases}$$

Figure 2:
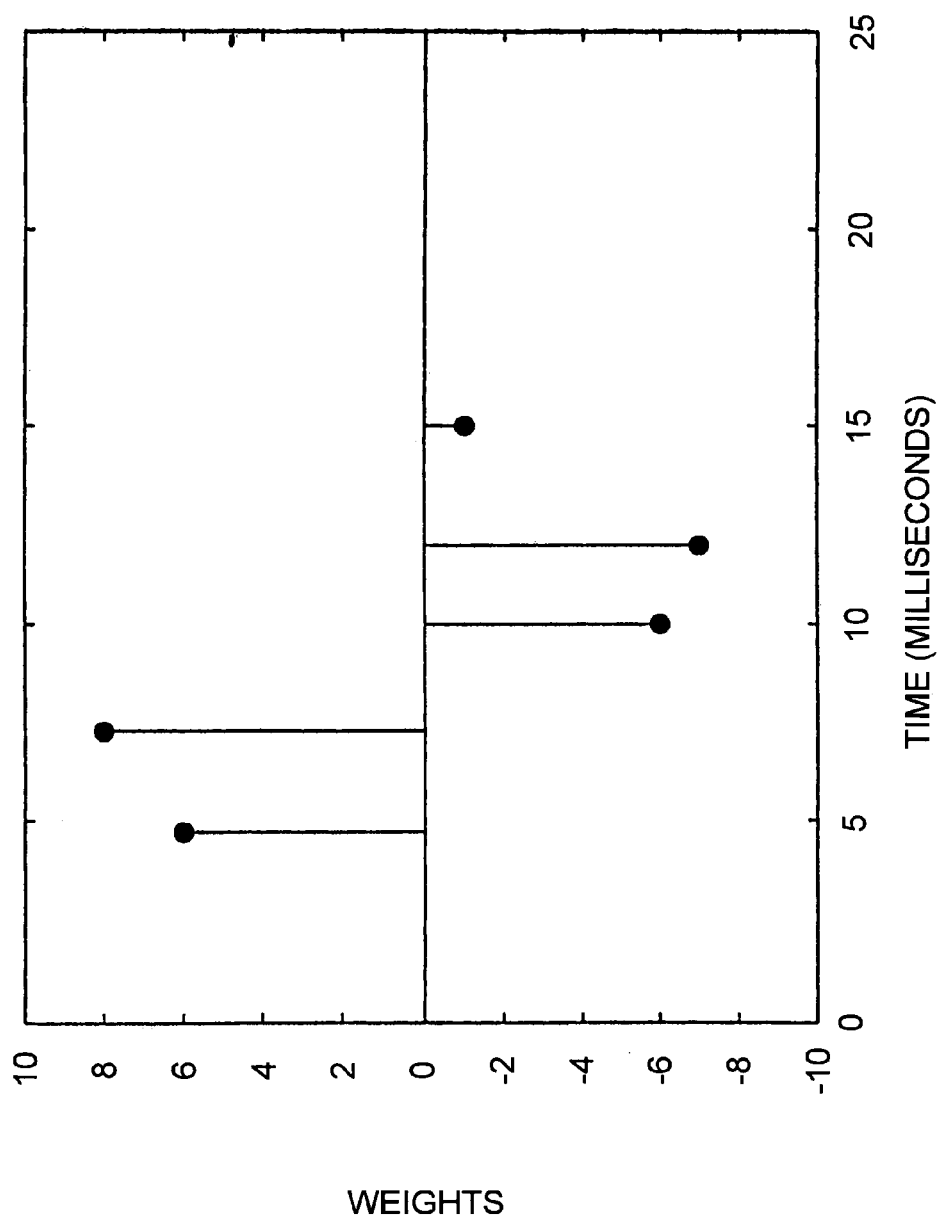
FIG. 2 illustrates a weighted ABR template.

The summed polarity sequence X is then compared with a template waveform, which has been compiled with the use of normative data (see FIG. 1). This template is comprised of M weighted points, strategically placed to match the typical ABR waveform (see FIG. 2). At each of the M points, a weight is assigned, reflecting the importance and polarity of the given measurement point in ascertaining the presence of an ABR, as derived from normative data. Thus, for any given point m, the sum of the polarities would be $x_m$. The sum of the weights equals zero.

The present invention uses a test statistic z to aid in determining if an ABR is present. This test statistic is defined as:

$$z = \frac{\sum_{m=1} w_m(x_m - \mu_x)}{\sqrt{Npq \sum_{m=1}^{M} w_m^2}}$$

where N is the number of sweeps, p is the probability of positive polarity, q is the complementary probability. The test statistic z scores the random binary array X by multiplying its elements $x_m$ at each template point m with the corresponding weight $w_m$, and summing these results into a single, normalized number. Now, in the absence of an ABR, the peak of the distribution of z would remain at zero, while in the presence of an ABR, the test statistic would grow with increasing number of sweeps N.

Subjects exhibit variability in the latency of the ABR waveform, so that different subjects, each of whom can hear, may exhibit ABR waveforms at different times after the click stimulus. In order to compensate for this variability, the test statistic z may be recalculated at various times. The highest z from each of these time-shifted samples, $z_{max}$, can be saved and used to determine the presence of the ABR. In a preferred embodiment of the present invention, a pass is indicated when $z_{max}$ reaches a value that is 4 standard deviations from zero.

Additionally, it has been found that the peak-to-peak amplitude of the ABR in normal-hearing babies varies from baby to baby. As explained below, the present invention accounts for this variability in ABR amplitude, by making conservative assumptions about the ABR amplitude of the subject who is being tested.

The present invention also discloses a method and apparatus for detecting excessive noise contribution, and for detecting non-physiological noise and determining when such non-physiological noise is excessive.

Excessive (symmetric) noise detection is achieved by calculating the EEG signal variance for each block of sweeps, defined as:

$$\begin{cases} \sigma_S^2 = \dfrac{\sum_{t=1}^{T}(S(t) - \mu_S)^2}{T-1} \\ \mu_S = \dfrac{\sum_{t=1}^{T} S(t)}{T} \end{cases}$$

Here T represents all sample points in all sweeps in the block and S(t) the EEG signal amplitude at sample time t. This signal variance is compared with a threshold signal variance derived from normative data. The variance threshold, corresponds to a level of noise so high that even a subject whose ABR was in the $90^{th}$ percentile in terms of amplitude would still fail 50% of the time.

Under the present invention, excessive noise evaluation is conducted only after the completion of each block of sweeps. When excessive noise is detected, the evaluation pauses, and the operator is asked whether he or she wants to continue evaluation, or stop the evaluation to allow time to address and possibly ameliorate the excessive noise.

The present invention also allows for the detection of excessive polarity bias in the response signal. Such polarity bias, β, is associated with certain non-physiological noise sources, such as the refresh function on a computer monitor. Excessive bias can skew the average sum of polarities. Excessive non-physiological (asymmetric) noise detection is achieved by calculating the EEG polarity bias for each block of sweeps, defined as:

$$\beta = \left| \frac{1}{T} \sum_{t=1}^{T} x(t) - \frac{1}{2} \right|$$

This polarity bias is compared with the threshold bias associated with the $10^{th}$ percentile ABR waveform, which is based on the signal variance and is derived from normative data.

Figure 4:
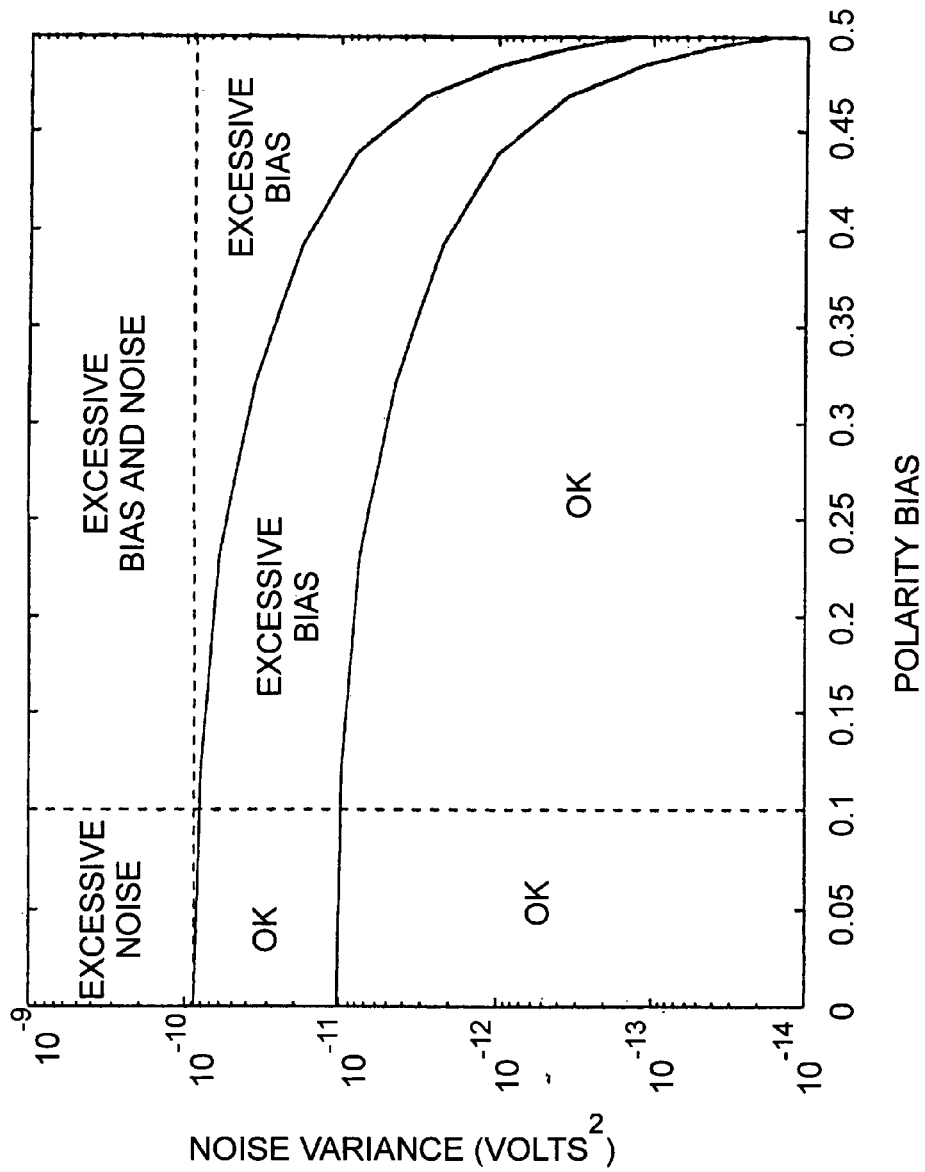
FIG. 4 illustrates excessive bias and noise detection thresholds as a function of signal noise and polarity bias.

Using normative data, along with the excessive noise techniques described, one is able to define regions of different combinations of noise variance and polarity bias, which are assigned with different test condition results, and which define adverse testing conditions (FIG. 4). In defining these regions of adverse testing conditions, the noise variances associated with the $10^{th}$ and $90^{th}$ percentile ABR waveform are used as the threshold curves for the excessive noise and bias detection.

In accordance with another aspect of the present invention, one can evaluate polarity bias after the completion of each block of sweeps. If excessive bias is indicated, the last block of sweeps may be rejected, and the operator may be queried as to whether the evaluation should continue, or should be suspended to address the excessive bias.

The polarity bias indicator of the present invention turns on every time the bias exceeds the minimum threshold, which is set at four standard deviations away from the mean of the no-bias condition. Other levels could be used. Since the sources of asymmetrical noise, and hence polarity bias, are commonly non-physiological in origin, the bias indicator can be used to detect the presence of certain types of electrical interference from environmental sources, even if the polarity bias does not significantly affect the progression of $z_{max}$.

The present invention also provides for an improved ability to detect excessive ambient acoustic noise. Research has indicated that ambient noise can mask the click stimulus. (See Jesteadt, et al., "Forward-Masking Functions," J. Acoust. Soc. Am., Vol. 71, No. 4 April 1982). In order to address this problem, in accordance with the present invention the signal energy, E, of the ambient noise is measured, rather than the amplitude of the signal. Additionally, the present invention gathers signal energy measurements in three approximately 20-millisecond windows, each placed immediately prior to the onset of one of the last three clicks. Excessive ambient noise is determined according to the following equation:

$$E = \Delta t \left[ \frac{1}{2} \sum_{T1} P(t) + \frac{1}{3} \sum_{T2} P(t) + \frac{1}{6} \sum_{T3} P(t) \right] \leq E_{threshold}$$

In this equation, T1, T2, and T3 are the pre-click windows of time associated with the current, previous and $2^{nd}$ previous click, respectively, $P_n(t)$ represents the filtered microphone signal at sample time t for sweep n, and $\Delta t$ represents the sample time interval ($\Delta t = 0.25$ milliseconds). If the weighted energy sum E exceeds a pre-set threshold, the current sweep is rejected and the rejection is noted through an indicator on the graphical user interface or otherwise.

The generation of the click stimulus, the detection of the EEG response signal, the detection of the ambient noise, the processing and analysis of the EEG response signal, and the display of the results are performed by conventional electronic means, e.g. digital microprocessor controlled devices. Such devices include a transducer to generate the auditory stimulus, conventional electrodes to detect the EEG response signal, a conventional microphone to detect the ambient noise. To analyze the EEG response signal a processing unit, such as a conventional microprocessor, and memory unit are needed. Additionally, a display unit and optionally an input device, such as a mouse and/or a keyboard, provide operator interface.

Figure 6:
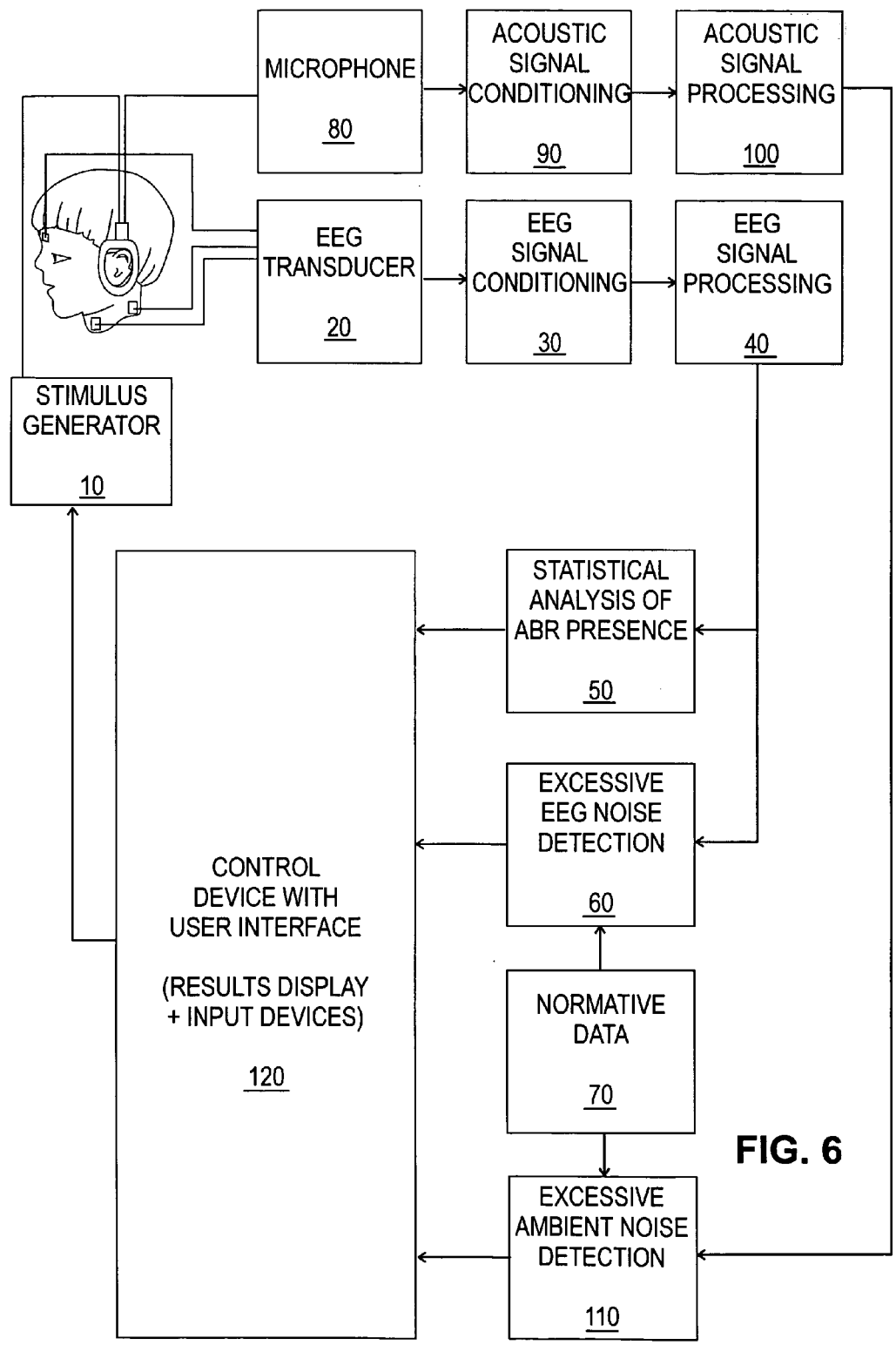
FIG. 6 is a block diagram of the components of the testing apparatus of the present invention.

As shown in FIG. 6, stimulus generator 10 generates the click stimulus, and EEG transducer 20 detects the EEG response to the stimulus. Next, EEG signal conditioning 30 and signal processing 40 occur, readying the EEG response for analysis. Statistical analysis for the presence of an ABR 50 then occurs, and excessive EEG noise detection 60 simultaneously occurs, in accordance with the present invention. Also during evaluation, microphone 80 detects ambient noise, and this ambient acoustic signal undergoes signal conditioning 90 and processing 100, and excessive ambient noise is detected 110, in accordance with the present invention. Normative data 70 is used for both the excessive ambient noise analysis and the excessive EEG noise detection. Finally, a control device with user interface 120 displays the results.

One skilled in the art will appreciate that the present invention can be practiced by other than the preferred embodiments, which are presented for purposes of illustration and not of limitation. In addition, the specific parameter values identified herein are useful or representative parameter values, and it should be understood that other values or ranges of values for these parameters may be used without departing from the spirit and scope of the invention.

We claim:

1. A device for hearing evaluation of a subject comprising:
   means for repeatedly delivering an auditory stimulus;
   means for sampling an EEG response to said stimulus;
   means for detecting when non-physiological noise is associated with said EEG response, for automatically determining the amount of said non-physiological noise, and for automatically determining when said amount is excessive relative to a threshold, wherein said threshold is derived from normative data; and
   pausing means for pausing the evaluation when said amount is excessive relative to said threshold.

2. A method for hearing evaluation of a subject, comprising the steps of:
   repeatedly delivering an auditory stimulus;
   measuring the EEG response to said stimulus;
   detecting the noise associated with said EEG response;
   automatically detecting the amount of said noise;
   automatically determining that said amount is excessive relative to a threshold, wherein automatically determining that said noise amount is excessive relative to a threshold comprises computing a composite signal noise variance;
   comparing said composite signal noise variance to a predetermined threshold; and
   determining that the composite signal noise variance is greater than said threshold.

3. The method according to claim 2, further comprising the step of pausing the testing in response to determining that said noise amount is excessive relative to a threshold.

4. The method according to claim 3, further comprising the step of determining if said EEG response contains an ABR waveform.

5. A method for hearing evaluation of a subject, comprising the steps of:
repeatedly delivering an auditory stimulus;
measuring EEG responses to said stimulus, said EEG responses having amplitudes;
detecting noise associated with said EEG responses;
determining a degree of polarity bias in said EEG responses;
determining when said bias is excessive relative to a threshold;
whereby determining when said polarity bias is excessive relative to a threshold comprises
digitizing said EEG response;
transforming said digitized EEG response into a series of binary numbers corresponding to the polarity of the amplitude of said EEG response;
transforming said binary numbers into an array of polarity sums;
determining the bias in said array of polarity sums; and
comparing said bias to a predetermined threshold.

6. The method according to claim 5, whereby determining when said polarity bias is excessive relative to a threshold comprises:
determining the difference between the mean and the median amplitude in said EEG responses; and
comparing said difference to a predetermined threshold.

7. The method according to claim 5, further comprising the step of pausing the testing in response to detecting excessive levels of polarity bias in said noise.

8. The method according to claim 5, further comprising the step of determining if said EEG response contains an ABR waveform.

9. A method for hearing evaluation of a subject, comprising the steps of:
repeatedly delivering an auditory stimulus;
measuring EEG response to said stimulus;
detecting the noise associated with said EEG response;
determining the amount of said noise;
determining the degree of polarity bias in said EEG response;
determining when adverse evaluation conditions are present, based upon both said noise amount and said noise polarity bias;
pausing the step of determining the degree of polarity bias in said EEG response.

10. A method for hearing evaluation of a subject which comprises the steps of:
repeatedly delivering an auditory stimulus to a subject;
measuring an EEG response to the stimulus said response having a amplitude polarity at each point in time;
digitizing said EEG response;
transforming said digitized EEG response into a series of binary numbers corresponding to the polarity of the amplitude of said EEG response;
transforming said binary numbers into an array of polarity sums;
detecting the noise associated with said EEG response;
determining the amount of said noise;
automatically detecting when said amount is excessive relative to a threshold;
accounting for any excessive amounts of said noise; and
determining if an EEG response contains an ABR waveform by comparing the array of polarity sums against normative data; wherein the step of accounting for excessive amounts of said noise comprises pausing the evaluation.

11. A method for hearing evaluation of a subject which comprises the steps of:
repeatedly delivering an auditory stimulus to a subject;
measuring an EEG response to the stimulus said response having a amplitude polarity at each point in time;
digitizing said EEG response;
transforming said digitized EEG response into a series of binary numbers corresponding to the polarity of the amplitude of said EEG response;
detecting the noise associated with said EEG response;
determining the amount of said noise;
automatically detecting when said amount is excessive relative to a threshold;
accounting for any excessive amounts of said noise; and
determining if an EEG response contains an ABR waveform by comparing the array of polarity sums against normative data,
wherein the step of accounting for excessive amounts of said noise comprises rejecting a portion of said array of polarity sums.

12. A method of evaluation for hearing loss which comprises the steps of:
repeatedly delivering an auditory stimulus to a subject;
measuring an EEG response to the stimulus said response having an amplitude polarity at each point in time;
digitizing said EEG response;
transforming said digitized EEG response into a series of binary numbers corresponding to the polarity of the amplitude of said EEG response;
transforming said binary numbers into an array of polarity sums;
detecting the noise associated with said EEG response;
detecting the degree of polarity bias in said EEG response;
determining when said bias is excessive relative to a threshold;
accounting for any excessive bias; and
determining if an EEG response contains an ABR waveform by comparing the array of polarity sums against normative data.

13. The method according to claim 12, wherein the step of accounting for any excessive polarity bias comprises pausing the evaluation.

14. The method according to claim 12, wherein the step of accounting for any excessive polarity bias comprises rejecting a portion of said array of polarity sums.

15. The method according to claim 5 wherein said noise comprises non-physiologic (asymmetric) noise and symmetric noise further comprising the step of detecting said non-physiologic (asymmetric) noise separate from said symmetric noise.

16. The method according to claim 9 wherein said noise comprises non-physiologic (asymmetric) noise and symmetric noise further comprising the step of detecting said non-physiologic (asymmetric) noise separate from said symmetric noise.

17. The method according to claim 12 wherein said noise comprises non-physiologic (asymmetric) noise and symmetric noise further comprising the step of detecting said non-physiologic (asymmetric) noise separate from said symmetric noise.

* * * * *